United States Patent [19]
Kusuda et al.

[11] Patent Number: 5,455,266
[45] Date of Patent: Oct. 3, 1995

[54] ENHANCED CHEMOTHERAPEUTIC COMPOSITIONS AGAINST MICROBIAL INFECTIONS IN FISH, THE PREPARATION AND USE THEREOF

[75] Inventors: Riichi Kusuda, Kochi, Japan; Ulrich Hamel, Ingelheim/Rhein, Germany

[73] Assignee: Boehringer Ingelheim Vetmedica GmbH, Ingelheim am Rhein, Germany

[21] Appl. No.: 119,932

[22] Filed: Sep. 10, 1993

[30] Foreign Application Priority Data

Sep. 11, 1992 [EP] European Pat. Off. .............. 92115559

[51] Int. Cl.$^6$ ...................... A61K 31/135; A61K 31/335
[52] U.S. Cl. .......................... 514/450; 514/649; 514/653; 514/659
[58] Field of Search .................... 514/450, 659, 514/649, 653

[56] References Cited

U.S. PATENT DOCUMENTS 4,705,803  11/1987  Kern et al. ............................... 514/450
4,918,108   4/1990  Kern et al. .

FOREIGN PATENT DOCUMENTS 0088943  3/1983  Germany .
0138020  9/1984  Germany .

OTHER PUBLICATIONS

T. Aoki, S. Sunao and T. Kitao, "The Bulletin of the Japanese Society of Scientific Fisheries", vol. 49, No. 11 (1983), 1673–1677.

The Journal of the British Veterinary Association, vol. 112, No. 8, Feb. 19, 1983.

CA 78 (1973), Abstract No. 11590d.

Arzneim.–Fosch. 31(6), 974–976 (1981).

Primary Examiner—Johann Richter
Assistant Examiner—Michael B. Hydorn
Attorney, Agent, or Firm—Robert P. Raymond; Alan R. Stempel; Mary-Ellen Devlin

[57] ABSTRACT

The invention relates to enhanced chemotherapeutic compositions against microbial infections in fish, containing a benzylamine derivative of general formula

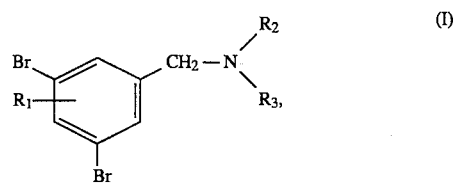

wherein $R_1$ to $R_3$ are defined as in claim 1, or a physiologically acceptable acid addition salt thereof and an effective amount of an antimicrobially active substance or a combination of such substances, preferably incorporated in feed, the preparation and the use thereof.

11 Claims, No Drawings

ENHANCED CHEMOTHERAPEUTIC COMPOSITIONS AGAINST MICROBIAL INFECTIONS IN FISH, THE PREPARATION AND USE THEREOF

U.S. Pat. Nos. 3,336,308, 3,536,713 and 4,113,777 describe benzylamine derivatives and the physiologically acceptable acid addition salts thereof with inorganic or organic acids which have secretolytic properties, as well as an antitussive effect; in particular the compounds
bromhexine hydrochloride (compound A=N-methyl-N-(2-amino- 3,5-dibromo-benzyl)-cyclohexylamine-hydrochloride), and
ambroxol hydrochloride (compound B=N-(2-amino-3,5-dibromo-benzyl)-trans- 4-hydroxy-cyclohexylamine-hydrochloride)
are described as secretolytics for therapeutic purposes and bromhexine hydrochloride as well as dembrexine hydrochloride (compound C=N-(3,5-dibromo-2-hydroxy-benzyl)-trans-4-hydroxy-cyclohexylamine-hydrochloride) also for veterinary purposes.

Australian Patent No. 570,070 describes benzylamines of general formula

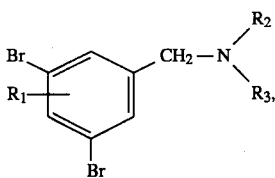

wherein
$R_1$ represents a hydroxy group in the 2- or 4-position or an amino group in 2-position,
$R_2$ represents a hydrogen atom or a methyl or ethyl group and,
$R_3$ represents a cyclohexyl or hydroxy-cyclohexyl group, and the physiologically acceptable acid addition salts thereof with inorganic or organic acids, as compounds which inhibit or prevent on patients the colonisation of surfaces by microorganisms, particularly in the oral and pharyngeal cavity, in the lungs, in the urogenital tract, in the mammary glands, on the skin and in the conjunctival membranes.

Moreover, Australian Patent No. 562,014 describes a method of enhancing the resorption of an antibacterially active substance or combination, administered parenterally, into the tissue of a human or animal, suitably mammalian, body which method comprises the parenteral administration, preferably together with the said antibacterially active substance or combination, of at least 0,1 mg/kg body weight of a compound of general formula I as hereinbefore defined. This patent describes only the treatment of mammals and no report has been published on the treatment of fish.

Surprisingly, it has now been found, when the above-mentioned benzylamine derivatives of general formula I are administered to fish, together with an antimicrobially active substance or a combination thereof the chemotherapeutic activity of the antimicrobially active substance or combination is enhanced.

According to one aspect of the present invention there is provided a method of enhancing the chemotherapeutic activity of an antimicrobially active substance or a combination thereof administered to fish, which method comprises the peroral administration, preferably together with the said antimicrobially active substance or a combination of such substances, of at least 0.1 mg/kg body weight of a compound of general formula

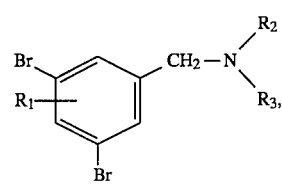

(wherein $R_1$, $R_2$ and $R_3$ are as hereinbefore defined) or a physiologically acceptable acid addition salt thereof.

According to a further aspect of the present invention there is provided a suitable feed for fish, containing a compound of formula I (as defined above) or a physiologically acceptable acid addition salt thereof together with an antimicrobially active substance or a combination of such substances selected from the following:

an antimicrobial agent which is absorbed in the digestive tract of fish, such as an antibotic of the tetracycline, macrolide, chloramphenicol or β-lactam group, or a synthetic antimicrobial active substance of the sulfonamide, nitrofurane or quinolone group, or a sulphonamide in combination with an agonist, and a physiologically acceptable acid addition salt thereof.

According to get a further aspect of the present invention there is provided the use of a compound of formula I (as defined above) or a physiologically acceptable acid addition salt thereof for enhancing the activity of an antimicrobially active substance or a combination of such substances administered perorally to fish.

The invention thus finds particular use in connection with the treatment of fish suffering from infections caused by bacteria such as Aeromonas hydrophila, Aeromonas salmonicida, Aeromonas spp., Edwardsiella spp., Edwardsiella tarda, Enterococcus seriolicida, Enterococcus sp., Flavobacterium branchiophilum, Flexibacter columnaris, Flexibacter maritimus, Listonella anguillarum, Mycobacterium marinum, Mycobacterium sp., Nocardia seriolae, Pasteurella piscicida, Pasteurella sp., Pseudomonas anguilliseptica, Pseudomonas fluorescens, Pseudomonas putida, Pseudomonas spp., Renibacterium salmoninarum, Salmonella spp., Staphylococcus epidermidis, Streptococcus iniae, Streptococcus spp. and Vibrio spp.

The invention also finds use in the prevention or prophylaxis of infections of fish, especially there caused by primary and secondary bacterial infections or predisposing stress.

Thus, as a result of the enhancement of the activity of an antimicrobial compound better and safer therapeuctic results can be obtained and the quantity of an antimicrobial compound administered can be reduced in comparison to the quantity required when the substance or combination in question is administered on its own and consequently a significant cost saving can be achieved. Moreover, the problem of residues is lessened since the necessary amount of an antimicrobial agent can be reduced according to the invention.

Examples for suitable fish species, which may be treated according to the invention are the following:

fishes such as yellow-tail, salmon, trout, eel, carp, sea bream, tilapia, shell fish, Crustacea, tench or pike, hobby fishes such as ornamental fish or aquarium fish, e.g. goldfish, and koi.

Preferred compounds of formula I include those wherein $R_2$ and $R_3$ together with the nitrogen atom to which they are attached represent N-methyl-cyclohexylamino, N-ethyl-cyclohexylamino, trans-4-hydroxy-cyclohexylamino or cis-3-hydroxy-cyclohexylamino groups.

Particularly preferred benzylamine derivatives of formula I are the compounds
N-methyl-N-(2-amino-3,5-dibromo-benzyl)-cyclohexylamine,
N-(2-amino-3,5-dibromo-benzyl)-trans-4-hydroxy-cyclohexylamine,
N-(3,5-dibromo-4-hydroxy-benzyl)-cis-3-hydroxy-cyclohexylamine and
N-(3,5-dibromo-2-hydroxy-benzyl)-trans-4-hydroxy-cyclohexylamine,
and the physiologically acceptable acid addition salts thereof with inorganic or organic acids.

An antibacterially active substance or combination suitable for use in the various aspects of the invention, possibly in the form of one of its esters or physiologically acceptable salts, may be for example selected from the following:

- an antibiotic of the tetracycline group (e.g. oxytetracycline, oxytetracycline hydrochlorid, rolitetracycline and doxycycline);
- a macrolide (e.g. erythromycine and novobiocin);
- an antibiotic of the β-lactam group (e.g. procaine penicillin, benethamine penicillin, benzathine penicillin, the benzathine salts of oxacillin, cloxacillin or ampicillin, and the cephalosporins);
- a quinolone (e.g. nalidixic acid, oxolinic and flumequine);
- a sulphonamide or a sodium salt thereof (e.g. sulphadiazine, sulphadoxine, sulphamethoxazole, sulphadimethoxine, sulphadimidine and sulphathiazole), or
- a sulphonamide in combination with an agonist (such as trimethoprim), e.g. a sulphadimidine-sulphathiazole-trimethoprim combination, or a combination of the salts thereof.

Preferred feed compositions include those containing
bromhexine hydrochloride (compound A),
ambroxol hydrochloride (compound B), and
dembrexine hydrochloride (compound C),
or a physiologically acceptable acid salt thereof and one of the above-mentioned antimicrobial substances or combinations.

Particularly preferred feed composition include those containing bromhexine-hydrochloride and
an antibiotic of the β-lactam group (e.g. ampicillin).

By way of example, to demonstrate the antimicrobially enhancing effect achieved with the various aspects of the invention the effect of bromhexine hydrochloride (compound A) containing feed were tested against induced pseudotuberculosis in yellow-tail in the following manner:

Method I

Experimental fish: Young yellow-tails, weighing 29.4 g on average.

Rearing for fish: The treatment groups were reared in plastic containers of 800 l capacity with continuous water flow and fed on frozen fish chops twice a day in an amount of up to 12% of body weight. Water temperature ranged from 26.8° to 27.6° C. during the trial.

Treatment groups: Prior to the trial, fish were acclimatized for a week and maximum feed intake was measured before allocation into treatment groups. Groups consisting of 35 yellow tails each were treated with either

- 0 mg/kg body weight of compound A+10 mg/kg of ampicillin (group No. 1),
- 1 mg/kg body weight of compound A+10 mg/kg of ampicillin (group No. 2),
- 5 mg/kg body weight of compound A+10 mg/kg of ampicillin (group No. 3), or
- 0 mg/kg body weight of compound A+0 mg/kg of ampicillin (groups Nos. 4 and 5).

Administration of test materials: The test materials, a binder (Stash, Dai-Nippon Pharma.) and fresh fish mince were mixed at the prescribed levels and fed ad libitum to experimental fish at 10:00 a.m. every day. Feed was limited to 6% of body weight.

Experimental infection: Water suspension (10 3.4 cfu/ml) was prepared from 24 hours culture on a BHI agar plate of *Pasteurella piscicida* OT-8447. Fish were immersed in the water suspension for five minutes with aeration to establish the infection. The fish were observed for 10 days after the infection and dead fish were sacrificed and relevant kidney samples cultured for isolation of pathogenic microorganisms.

The trial results were summarized in the following table:

| Treatment group | Days after infection/number of deaths | | | | | | | | | | survived in % |
|---|---|---|---|---|---|---|---|---|---|---|---|
| | 1 | 2 | 3 | 4 | 5 | 6 | 7 | 8 | 9 | 10 | |
| No. 1 | 0 | 0 | 0 | 0 | 4 | 3 | 3 | 0 | 0 | 0 | 64.3 |
| No. 2 | 0 | 0 | 0 | 0 | 1 | 0 | 1 | 0 | 0 | 0 | 93.9 |
| No. 3 | 0 | 0 | 0 | 0 | 5 | 4 | 7 | 1 | 0 | 0 | 48.6 |
| No. 4 | 0 | 0 | 0 | 5 | 7 | 7 | 2 | 1 | 0 | 0 | 26.7 |
| No. 5 | 0 | 0 | 0 | 4 | 10 | 9 | 3 | 3 | 1 | 0 | 10.9 |

Method II

Experimental fish: Young yellow-tail, weighing 45.7 g in average.

Accommodation and feeding: Fish were grouped in plastic containers with continous water flow and fed on minced sand launce at a rate of 12% of body weight divided into twice feedings a day.

Administration of compound A: Predetermined aliquots of compound A and ampicillin technical powders were mixed in a thickner (Stash, Dainippon Pharm. Co., 1,5% to feed), then the mixtures were thoroughly mixed in minced sand launce by the aid of a mechanical mixer.

Feed intake was measured in advance and the experimental feeds were given ad libitum until engorged.

Artifical induction of the infection: Cultures of ampicillin-sensitive *Pasteurella piscida*, strain OT-8447 were suspended in sea water at the rate of $10^3$ CFU/ml. Experimental fish were submerged in the water for five minutes.

Treatment groups: compound A was administered for five days prior to the infection, while ampicillin was orally given in feed for three days starting immediately after the infection. The treatments were shown below:

| Treatment codes | compound A mg/kg body weight pro day | Ampicillin mg/kg body weight pro day |
|---|---|---|
| 1 | 1 | 0 |
| 2 | 2 | 0 |
| 3 | 1 | 10 |
| 4 | 0 | 10 |
| 5 | 0 | 0 |

Measurements of body-defense factors: Lyzozyme activities in mucus of body surface and blood serum, hemoagglutination titers (HA) and amounts of antibody were measured according to the methods of Salati et al. (see F. Salati, M. Hamaguchi and Riichi Kusuda: Fish Pathol. 22, 93–98 (1987)). Phagocytosis of renal cell (PI), chemotaxic factor (CTF) and, superoxide activity (SO) and myelo-peroxidase activity (MPO) were measured after the methods of Kusuda et al. (see R. Kusuda, M. Ninomiya, M. Hamaguchi, A. Muraoka: Fish Pathol. 23, 191–196 (1988)), Boyden (see S. V. Boyden: J. Exp. Med. 115, 453–462 (1962)) and Yamaguchi/Kakinuma (see T. Yamaguchi and K. Kakinuma: Experimental Methods of White Blood Cells, Edited by Ensho Project, Torinshoken, 79–82 (1979)), respectively.

The results were summarized in the following tables:

TABLE 1

Effects of compound A and ampicillin on induced pseudotuberculosis in yellow-tail

| Treatment codes | No. death after days of the induction | | | | | | | | | | Dead/Total |
|---|---|---|---|---|---|---|---|---|---|---|---|
| | 1 | 2 | 3 | 4 | 5 | 6 | 7 | 8 | 9 | 10 | |
| 1 | 0 | 0 | 0 | 2 | 4 | 3 | 1 | 1 | 0 | 1 | 12/30 |
| 2 | 0 | 0 | 0 | 1 | 5 | 2 | 1 | 2 | 0 | 0 | 11/30 |
| 3 | 0 | 0 | 0 | 0 | 0 | 0 | 0 | 0 | 0 | 0 | 0/30 |
| 4 | 0 | 0 | 0 | 1 | 2 | 1 | 0 | 1 | 0 | 0 | 5/30 |
| 5 | 0 | 0 | 1 | 2 | 4 | 4 | 2 | 1 | 0 | 1 | 14/30 |

TABLE 2

Activities body-defense parameters in yellow-tail with and without compound A

| Treatment codes | Lyzozyme (u/ml) | HA (1:x) | Antibody (μg/ml) | SO (%) | MPO (%) | PI | CTF (%) |
|---|---|---|---|---|---|---|---|
| 1 | 5.38 | 4 | 496 | 105 | 98 | 4.82 | 95 |
| 2 | 5.42 | 4 | 465 | 110 | 105 | 4.25 | 89 |
| 3 | 5.38 | 4 | 488 | 99 | 98 | 4.28 | 98 |
| 4 | 4.99 | 4 | 478 | 101 | 99 | 4.58 | 111 |
| 5 | 5.18 | 4 | 517 | 100 | 100 | 4.78 | 100 |

Discussion

Anti-infective activity of yellow-tail against pseudotuberculosis was not increased by single administrations of compound A, while an increase was suggested by an administration of compound A and ampicillin. Parameters of body-defense activities were not affected by compound A.

It is known that compound A is capable of increasing the excretion of mucus in mammals. Also it has been known that mucus on the body surface of fish plays an important role in the prophylaxis of pseudotuberculosis. However, it can be seen from the above results that compound A alone does not increase body-defense activity in fish, but is capable in combination with ampicillin of increasing the effectiveness of that compound.

The benzylamine derivatives of formula I used according to the invention and the physiologically acceptable acid addition salts thereof with inorganic or organic acids are well tolerated, because at the dose of 2.000 mg/kg no toxic side effects were observed.

In view of the above-mentioned biological characteristics, the benzylamine derivatives of formula I and the physiologically acceptable acid addition salts thereof are suitable, as already mentioned, for improving the activity of antimicrobial substances or combinations administered perorally to fish. The dosage is appropriately above 0.1 mg/kg, preferably between 1.0 and 2.0 mg/kg body weight daily.

The benzylamine derivative may, however, be administered in a separate therapeutic dose followed by a separate dose of the antibacterial substance or combination.

The active substances may be administered as single doses one or more times a day at regular or irregular intervals, preferably once or twice a day, as an additive to the bath, but particularly preferred, however, added to the feed.

Thus, for example, a suitable feed composition may conveniently contain 0.1 to 2 parts by weight of the compound of formula I or a physiologically acceptable acid addition salt thereof and an effective amount of an antimicrobial compound or a combination thereof. The amount of antimicrobial substance or substances used will depend upon their identity and can readily be determined by anyone skilled in the art.

Thus one dosage unit of the active compounds contained in a suitable feed composition or the concentration of the substances when administered in form of a single additive to the bath for treatment of fish suffering from bacterial infections may include the range of 0,5 to 1,5 mg/kg of compound A and
20 to 40 mg/kg of amoxicillin,
5 to 20 mg/kg of ampicillin,
3 to 4 ppm of colistin sulfate (in bath),
20 to 50 mg/kg of doxycycline hydrochloride,
25 to 50 mg/kg of erythromcin, 5 to 10 mg/kg of florfenicol,
10 to 20 mg/kg of flumequine,
40 to 50 mg/kg of josamycin,
50 to 80 mg/kg of kitasamycin
20 to 40 mg/kg of lincomycin hydrochloride,
40 to 60 mg/mg of miloxacin,
20 to 30 mg/kg of nalidixic acid,
40 to 50 mg/kg of nifurstyrenate, sodium,
40 to 50 mg/kg of novobiocin, sodium,
1 to 30 mg/kg of oxolinic acid,
5 to 10 ppm of oxolinic acid (in bath),
40 to 50 mg/kg of oxytetracycline, alkyltrimethylammonium-calcium,
40 to 50 mg/kg of oxytetracycline hydrochloride,
10 to 20 mg/kg of piromidic acid,
25 to 40 mg/kg of spiramicin embonate,
50 to 200 mg/kg of sulfamonomethoxine or sulfamonomethoxine, sodium,
7,5 to 15 mg/kg of sulfamonomethoxine in combination with 2,5 to 5 mg/kg of ormethoprim,
100 to 200 mg/kg of sulfisozole or sulfisozole, sodium,
50 to 200 mg/kg of sulfadimethoxine or sulfadimethoxine, sodium
10 to 60 mg/kg of thiamphenicol,
30 to 40 mg/kg of tetracycline hydrochloride, or
0,5 to 1,5 mg/kg of compound B and 20 to 40 mg/kg of amoxicillin,
5 to 20 mg/kg of ampicillin,
3 to 4 ppm of colistin sulfate (in bath),
20 to 50 mg/kg of doxycycline hydrochloride,
25 to 50 mg/kg of erythromcin,
5 to 10 mg/kg of florfenicol,
10 to 20 mg/kg of flumequine,
40 to 50 mg/kg of josamycin,
50 to 80 mg/kg of kitasamycin
20 to 40 mg/kg of lincomycin hydrochloride,
40 to 60 mg/mg of miloxacin,
20 to 30 mg/kg of nalidixic acid,
40 to 50 mg/kg of nifurstyrenate, sodium,
40 to 50 mg/kg of novobiocin, sodium,
1 to 30 mg/kg of oxolinic acid,
5 to 10 ppm of oxolinic acid (in bath),
40 to 50 mg/kg of oxytetracycline, alkyltrimethylammonium-calcium,
40 to 50 mg/kg of oxytetracycline hydrochloride,
10 to 20 mg/kg of piromidic acid,
25 to 40 mg/kg of spiramicin embonate,
50 to 200 mg/kg of sulfamonomethoxine or sulfamonomethoxine, sodium,
7,5 to 15 mg/kg of sulfamonomethoxine in combination with 2,5 to 5 mg/kg of ormethoprim,
100 to 200 mg/kg of sulfisozole or sulfisozole, sodium,
50 to 200 mg/kg of sulfadimethoxine or sulfadimethoxine, sodium
10 to 60 mg/kg of thiamphenicol,
30 to 40 mg/kg of tetracycline hydrochloride, or
0,5 to 1,5 mg/kg of compound C and
20 to 40 mg/kg of amoxicillin,
5 to 20 mg/kg of ampicillin,
3 to 4 ppm of colistin sulfate (in bath),
20 to 50 mg/kg of doxycycline hydrochloride,
25 to 50 mg/kg of erythromcin,
5 to 10 mg/kg of florfenicol,
10 to 20 mg/kg of flumequine,
40 to 50 mg/kg of josamycin,
50 to 80 mg/kg of kitasamycin
20 to 40 mg/kg of lincomycin hydrochloride,
40 to 60 mg/mg of miloxacin,
20 to 30 mg/kg of nalidixic acid,
40 to 50 mg/kg of nifurstyrenate, sodium,
40 to 50 mg/kg of novobiocin, sodium,
1 to 30 mg/kg of oxolinic acid,
5 to 10 ppm of oxolinic acid (in bath),
40 to 50 mg/kg of oxytetracycline, alkyltrimethylammonium-calcium,
40 to 50 mg/kg of oxytetracycline hydrochloride,
10 to 20 mg/kg of piromidic acid,
25 to 40 mg/kg of spiramicin embonate,
50 to 200 mg/kg of sulfamonomethoxine or sulfamonomethoxine, sodium,
7,5 to 15 mg/kg of sulfamonomethoxine in combination with 2,5 to 5 mg/kg of ormethoprim,
100 to 200 mg/kg of sulfisozole or sulfisozole, sodium,
50 to 200 mg/kg of sulfadimethoxine or sulfadimethoxine, sodium
10 to 60 mg/kg of thiamphenicol,
30 to 40 mg/kg of tetracycline hydrochloride.

Preferred feed compositions may contain
0,5 to 1,5 mg/kg of compound A and
5 to 20 mg/kg of ampicillin or
25 to 50 mg/kg of erythromycin or
1 to 30 mg/kg of oxolinic acid or
40 to 50 mg/kg of oxytetracycline hydrochloride or
50 to 200 mg/kg of sulfadimethoxine or sulfadimethoxine, sodium, or
0,5 to 1,5 mg/kg of compound B and
5 to 20 mg/kg of ampicillin or
25 to 50 mg/kg of erythromycin or
1 to 30 mg/kg of oxolinic acid or
40 to 50 mg/kg of oxytetracycline hydrochloride or
50 to 200 mg/kg of sulfadimethoxine or sulfadimethoxine, sodium, or
0,5 to 1,5 mg/kg of compound C and
5 to 20 mg/kg of ampicillin or
25 to 50 mg/kg of erythromycin or
1 to 30 mg/kg of oxolinic acid or
40 to 50 mg/kg of oxytetracycline hydrochloride or
50 to 200 mg/kg of sulfadimethoxine or sulfadimethoxine, sodium.

Particularly preferred feed compositions may contain
0,5 to 1,5 mg/kg of compound A and
5 to 20 mg/kg of ampicillin.

The type of animals feed in which the active substances may be incorporated at prescribed levels by common known and suitable mixing techniques, optionally together with auxiliary substances, for example extenders such as soya bean protein, lactose, brewer's yeast and limestone, diluents such as water, disolving intermediaries such as benzyl alcohol and n-butanol, thickeners such as hydroxypropyl methylcellulose, and pH-regulators such as pottasium hydroxide, sodium hydroxide, lactic acid, hydrochloric acid, acetic acid and propionic acid, and further additives such as vitamines and preservatives, depends on species as well as age of the fish and both type and size of the production unit.

The industrially manufactured feed formulations can be in mash, pelleted and extruded form and may comprise protein in the range of 40 to 54%, 4 to 11% fat, 1 to 3% fibre and 8 to 18% ash.

For example the complete feed for trouts in which the active substances may be incorporated may consist of pellets, 3 mm, specified as follows:
Ingredients
44% Crude Protein
2,8% Lysine
8% Crude Fat
2% Crude Fibre
9,5% Crude Ash
Additives Per kg Complete Feed
20,000 i.U. Vit. A
2,000 i.U. Vit. $D_3$
100 mg Vit. E
Propionic acid, Antioxidant BHT
Composition
Fishmeal, wheat white shorts, soyabean steamed, meat and bone meal, feather meal hydrol., partly delactosed dried whey, blood meal, sugar beet molasses, mineral/additive-premix.

What is claimed is:

1. A method for treating or preventing microbial infections in fish which comprises peroral administration to fish a mixture of:

a) a benzylamine derivative of the formula I

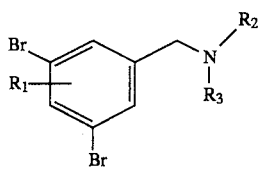

wherein
- $R_1$ represents a hydroxy group in the 2- or 4-position or an amino group in 2-position,
- $R_2$ represents a hydrogen atom or a methyl or ethyl group and,
- $R_3$ represents a cyclohexyl or hydroxy-cyclohexyl group, or a physiologically acceptable acid addition salt thereof, b) an effective mount of an antimicrobially active substance, and c) a suitable feed for fish.

2. A method for treating or preventing microbial infections in fish, as claimed in claim 1, wherein the feed contains a protein source for fish.

3. A method for treating or preventing microbial infections in fish, as claimed in claim 1, wherein:
a) in said benzylamine derivative of the formula I, $R_2$ and $R_3$ together with the nitrogen atom to which they are attached, represent a N-methyl-cyclohexylamino, N-ethyl-cyclohexylamino, trans-4-hydroxy-cyclohexylamino or cis-3-hydroxy-cyclohexylamino group, and
b) said antimicrobially active substance is selected from the group consisting of:
  i) antibiotics belonging to the group consisting of the tetracyclines, the macrolides, chloramphenicol, and the β-lactams;
  synthetic antimicrobials belonging to the group consisting of the sulfonamides, the nitrofuranes, and the quinolones group; and,
  iii) a sulphonamide in combination with an agonist.

4. A method for treating or preventing microbial infections in fish, as claimed in claim 3, wherein said benzylamine is selected from the group consisting of:
  N-methyl-N-(2-amino-3,5-dibromo-benzyl)-cyclohexylamine;
  N-(2-amino-3,5-dibromo-benzyl)-trans-4-hydroxy-cyclohexylamine;
  N-(3,5-dibromo-4-hydroxy-benzyl)-cis-3-hydroxy-cyclohexylamine;
  N-(3,5-dibromo-2-hydroxy-benzyl)-trans-4-hydroxy-cyclohexylamine; and the physiologically acceptable acid addition salts thereof.

5. A method for treating or preventing microbial infections in fish, as claimed in claim 4, wherein said benzylamine is N-methyl-N-(2-amino-3,5-dibromo-benzyl)-cyclohexylamine, or a physiologically acceptable acid addition salt thereof.

6. A method for treating or preventing microbial infections in fish, as claimed in claim 1 wherein said antimicrobially active substance is an antibiotic of the β-lactam group.

7. A method for treating or preventing microbial infections in fish, as claimed in claim 3 wherein said antimicrobially active substance is an antibiotic of the β-lactam group.

8. A method for treating or preventing microbial infections in fish, as claimed in claim 4 wherein said antimicrobially active substance is an antibiotic of the β-lactam group.

9. A method for treating or preventing microbial infections in fish, as claimed in claim 5 wherein said antimicrobially active substance is an antibiotic of the β-lactam group.

10. A method for treating or preventing microbial infections in fish, as claimed in claim 1 wherein said benzylamine derivative is N-methyl-N-(2-amino-3,5-dibromo-benzyl)-cyclohexylamine, or a physiologically acceptable acid addition salt thereof and wherein said antimicrobially active substance is ampicillin.

11. A method for treating or preventing microbial infections in fish, as claimed in claim 1, wherein there is added to said mixture an auxiliary substances selected from the group consisting of extenders, diluents, dissolving intermediaries, thickeners, pH-regulators, vitamins, and preservatives, or mixtures thereof.

* * * * *